United States Patent [19]
Kato

[11] Patent Number: 5,132,002
[45] Date of Patent: Jul. 21, 1992

[54] ION ANALYZER

[75] Inventor: Yoshiaki Kato, Mito, Japan

[73] Assignee: Hitachi, Ltd., Tokyo, Japan

[21] Appl. No.: 416,430

[22] Filed: Oct. 3, 1989

[30] Foreign Application Priority Data

Oct. 5, 1988 [JP] Japan .................... 63-249860

[51] Int. Cl.$^5$ .................................. G01N 27/26
[52] U.S. Cl. ............................ 204/416; 204/421
[58] Field of Search .............. 204/164, 400, 153.1, 204/416, 192.31, 421

[56] References Cited

U.S. PATENT DOCUMENTS

| | | | |
|---|---|---|---|
| 4,152,478 | 5/1979 | Takagi | 204/192.31 |
| 4,209,696 | 6/1980 | Fite | 250/281 |
| 4,298,795 | 11/1981 | Takeuchi et al. | 250/282 |
| 4,528,085 | 7/1985 | Kitajima et al. | 204/416 |

Primary Examiner—John Niebling
Assistant Examiner—Bruce F. Bell
Attorney, Agent, or Firm—Antonelli, Terry, Stout & Kraus

[57] ABSTRACT

A liquid containing ions is introduced onto the surface of an electrode, gas is supplied so that the liquid is moved while being held between the gas and the electrode, an electric field is applied so that the ions are extracted from the liquid, and the extracted ions are detected.

17 Claims, 6 Drawing Sheets

ION ANALYZER

BACKGROUND OF THE INVENTION

The present invention relates to an analyzer for ions in a liquid. and particularly to an apparatus suitable for analyzing ions in an effluent from a separation column.

When a liquid containing ions is discharged from a capillary to which a high voltage is applied, the liquid is in a conical form, and charged droplets are emitted with a good directivity from the tip of the conical form. A phenomenon wherein ions contained in a liquid are drawn out as droplets therefrom and nebulized by an electric field is known as EHD (Electrohydrodynamic Ionization). This phenomenon requires no heating of the liquid during nebulization and thus causes no thermal decomposition of thermally labile substances such as amino acids and nucleic acids, which are structural materials of protein and genes, respectively, and which are known as polar molecules.

This technique is capable of spraying a liquid at a rate of several $\mu l/min$. However, the maximum allowable flow rate of this technique is too low to be applied to an ion extractor used for mass-analyzing ions in an effluent discharged from a separation column used in liquid chromatography. It is therefore necessary to split an effluent from a semi-micro column ($<100\ \mu l/min$) or a packed column ($>100\ \mu l/min$) in 100 to 1000 parts. Such a split, however, cannot be easily performed and causes a significant deterioration of the overall sensitivity of the system.

An improvement of the above-mentioned EHD ionization has been proposed. This is described in Analytical Chemistry, Vol.59, No.22, Nov. 15, 1987, pp. 2692-2646.

In this improved method, a fused-silica capillary having an internal diameter of 50 $\mu m$ is inserted into a stainless steel capillary having an internal diameter of 0.2 mm, these capillaries being further inserted into a Teflon tube having an internal diameter of 0.8 mm. Dry nitrogen gas is caused to flow at a rate of 216 m/sec and at a pressure of 2.5 atm between the stainless steel capillary and the Teflon tube. A voltage of 3 KV is applied to the stainless steel capillary, and a voltage of 600 V is applied to an electrode opposing the stainless steel capillary. It has been reported that a fine mist: like smoke is generated from the fused-silica capillary when a liquid is caused to flow therethrough at several tens of $\mu l/min$.

It is thought that, in this technique, the nitrogen gas contributes to the stabilization of a conical form of liquid and the micronization of droplets owing to collision therewith, this being the main cause for an increase in the flow rate.

However, the results of experiments show that it is difficult to stably spray a liquid at a flow rate of 100 $\mu l/min$ or more and extract ions therefrom even by this technique. This technique is therefore unsatisfactory for a packed column (100 $\mu l/min$ or more) which is the most frequently used in liquid chromatography.

SUMMARY OF THE INVENTION

It is an object of the present invention to provide an ion analyzer which is capable of effectively extracting ions from a liquid.

It is another object of the present invention to provide an ion analyzer which is capable of effectively extracting and detecting ions in a liquid.

An ion analyzer of the present invention comprises an electrode having a surface onto which a liquid containing ions is introduced, means for supplying gas so that the liquid is moved while being held between the gas and the electrode, means for generating an electric field so as to extract the ions, and means for detecting the ions extracted.

The liquid which is introduced onto the surface of the electrode and which contains ions is moved by using the gas while being held between the gas and the electrode. The ions contained in the liquid are emitted in the form of fine droplets in a space and extracted from the fine droplets, breaking through the surface layers of the droplets.

Since the liquid is moved by the gas while being held between the gas and the electrode, the evaporation of the liquid by the gas is accelerated. In addition, since the speed of movement of the liquid at the surface in contact with the gas is greater than the speed of movement of the liquid at the surface in contact with the electrode, the liquid is splashed at the liquid surface in contact with the gas, whereby promoting the generation of droplets.

In this way, the evaporation of the liquid is accelerated by the gas and the splashing and the formation of droplets are accelerated by the difference between the speeds of movement at both surfaces of the liquid, whereby the ions can be effectively extracted.

Further, when a voltage is applied to the electrode for the purpose of forming an electric field for extraction of ions, there is the tendency that ions having the same polarity as that of the electrode, i.e., ions to be extracted, gather on the liquid surface in contact with the gas, while a charge having the opposite polarity gathers on the liquid surface in contact with the electrode. As the droplets produced therefore contain a large amount of ions, the evaporation of the ions, i.e., the extraction of the ions, is further accelerated in combination with the Coulomb repulsion between respective ions.

The ions extracted are detected by a detector.

Other objects and characteristics of the present invention will be clarified by reading the description below with reference to the attached drawings.

DESCRIPTION OF PREFERRED EMBODIMENTS

Figure 1:
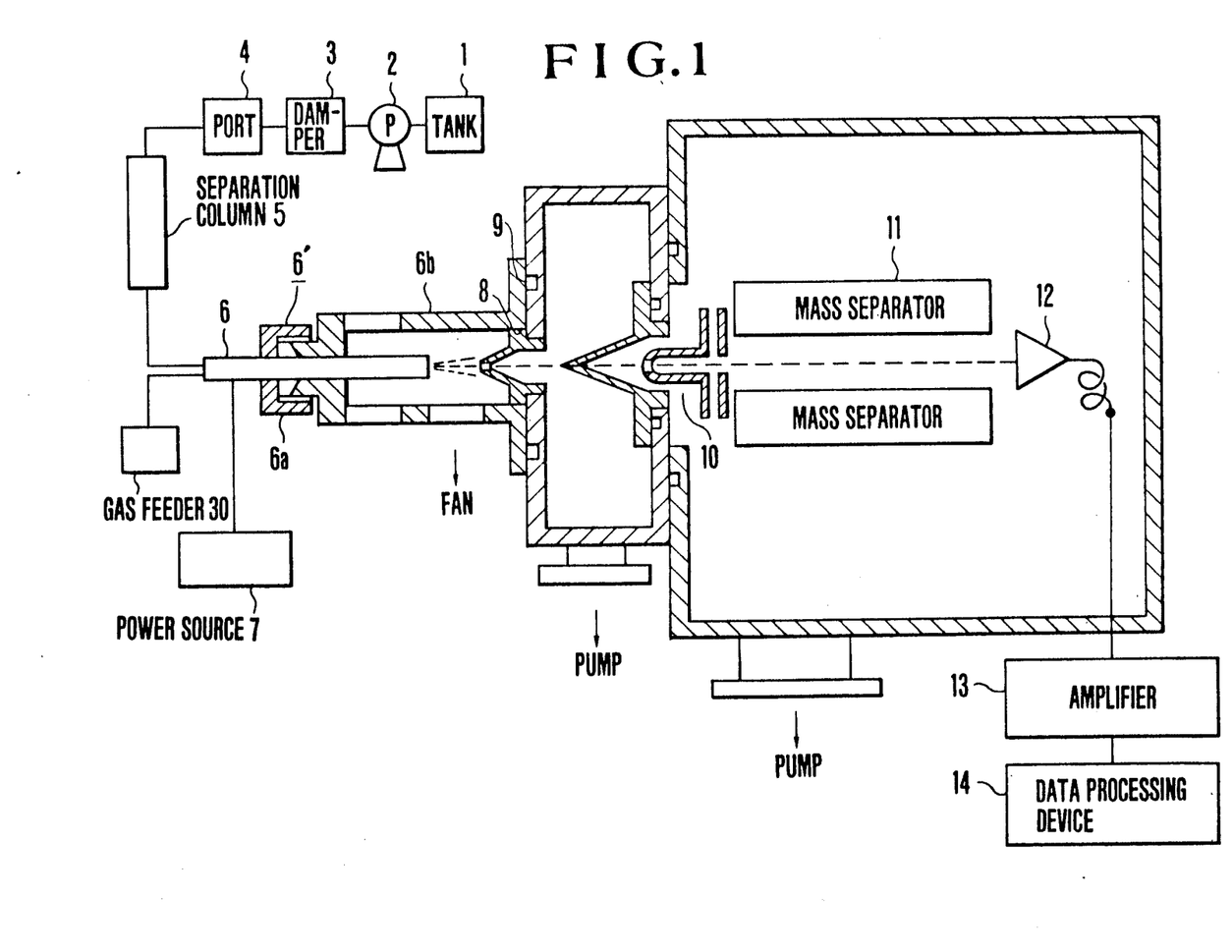
FIG. 1 is a sectional view of an ion analyzer in an embodiment of the present invention which is partially shown in a block form.

In FIG. 1, the elvant stored in an eluent storage tank 1 is sent to a separation column 5 through a damper 3 and a sample injection port 4 by a pump 2. The damper 3 is used for controlling the pulsating flow of the elvant caused by the pump 2.

The sample is added to or injected into the column 5 from the sample injection port 4 and separated during the process of passing the sample through the column 5 by using the eluent. The effluent from the column 5 is sent to an ion extractor 6'.

Figures 2A, 2B, 2C:
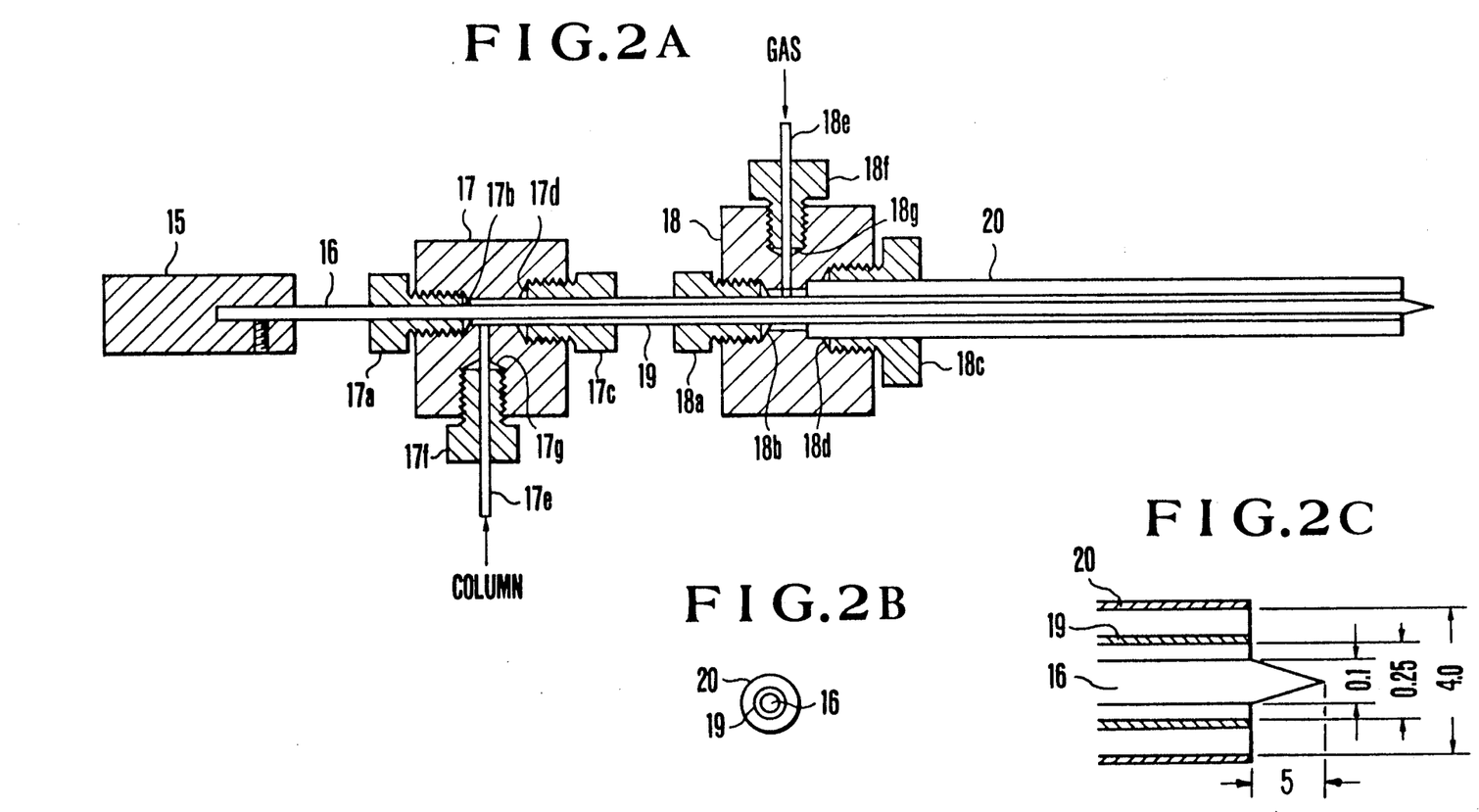
FIG. 2A is an enlarged sectional view of the ion extracting portion shown in FIG. 1.
FIG. 2B is a right side view of the needle-like electrode portion shown in FIG. 2A.
FIG. 2C is an enlarged sectional view of the tip of the needle-like electrode portion shown n FIG. 2A.

A nozzle portion 6 of the ion extractor 6' is mounted on the wall 6b of the extractor 6' by means of a nut 6a and is shown in detail in FIGS. 2A, 2B and 2C. In these drawings, a linear electrode, i.e., a needle-like electrode, 16 is passed through tees 17 and 18 and mounted on the tee 17 through a hermetic seal 17b by means of a nut 17a. The needle-like electrode 16 is preferably made of a stable material such as Pt, Au, C or the like for the purpose of preventing electrolysis. An insulating knob 15 is provided at one end of the needle-like electrode 16, with the other end being pointed. A first tube 19 is disposed around the needle-like electrode 16 and mounted to the tees 17 and 18 through hermetic seals 17d, 18b by means of nuts 17c and 18a, respectively. A second tube 20 is disposed around the first tube 19 and is mounted to the tee 18 through a hermetic seal 18d by means of a nut 18c. A tube 17e, which leads to the gap between the needle-like electrode 16 and the first tube 19, is mounted to the tee 17 through a hermetic seal 17g by means of a nut 17f and is connected to the lower end of the column 5 (FIG. 1). A tube 18e, which leads to the gap between the first tube 19 and the second tube 20, is mounted to the tee 18 through a hermetic seal 18g by means of a nut 18f and is connected to a gas feeder 30 (FIG. 1). To the needle-like electrode 16 is applied a high voltage from a power source 7 (FIG. 1). The tip of the linear electrode 16 projects from the end surfaces of the first and second tubes 19 and 20, and the amount (length) of projection of the electrode 16 can be adjusted by moving the needle-like electrode 16 by loosening the nut 17a.

Referring to FIGS. 1 and 2A-14 2C, the effluent sent to the ion extractor 6' from the column 5 passes through the tube 17e and leads to the gap between the needle-like electrode 16 and the first tube 19. The effluent is then sent to the tip of the needle-like electrode 16 by the sample sending gas, which is supplied from the gas feeder 30 through the tube 18e and the gap between the first and second tubes 19 and 20, while being subjected to contact with the gas. The gas feeder 30 allows an amount of the gas supplied to be adjusted. Inert gas such as argon or neon or gas such as nitrogen or oxygen can be used as the sample sending gas.

A high voltage is applied to the needle-like electrode 16 from the power source 7 so as to form an electric field between the needle-like electrode 16 and a first ion extracting electrode 8 at an earth potential for the purpose of extracting ions from the former electrode toward latter electrode. If the effluent contains ions, therefore, the combination of the force of the sample sending gas with the electrostatic force between the needle-like electrode 16 and the first ion extracting electrode 8 causes the ions contained in the effluent to be emitted as fine droplets from the tip of the needle-like electrode 16 against the liquid surface tension at the tip thereof and then extracted from the surfaces of the droplets. The thus-extracted ions pass through a small hole of the first ion extracting electrode 8 and then through a small hole of a second ion extracting electrode 9. The ions passing through the small hole of the second ion extracting electrode 9 are further drawn to a quadrupole mass separator 11 by an ion drawing electrode 10. The mass separator 11 has the function of selecting ions having a desired mass number, the ions selected being detected by a detector 12. The mass separator 11 is also capable of successively selecting ions having various mass numbers by sweeping mass numbers. The ions successively selected are successively detected by the detector 12. The detection signal output from the detector 12 is amplified by an amplifier 13 and led to a data processing device 14. The mass separator 11 may be of a magnet type.

The space between the needle-like electrode 16 and the first ion extracting electrode 8 is ventilated by using a fan (not shown) so that the gas staying in the space is discharged. The drawing electrode 10, the mass separator 11 and the detector 12 are disposed in a space which is evacuated to a given vacuum by using a vacuum pump (not shown). The space between the first and second ion extracting electrodes 8 and 9 is also evacuated to a given vacuum by using a vacuum pump (not shown).

As described above, the effluent passes through the gap between the needle-like electrode 16 and the first tube 19 and is then subjected to contact with the sample sending gas while being sent the tip of the needle-like electrode 16. The evaporation of the solvent contained in the effluent is thus accelerated, thereby increasing the concentration of the ions.

When the effluent is forced to be sent to the tip of the needle-like electrode 16 by the sample sending gas after passing through the gap between the needle-like electrode 16 and the first tube 19, the flow rate $v_3$ of the effluent on the side near the surface of the linear electrode is lower than the flow rate $v_2$ on the side of the liquid surface. This is because of the presence of friction between the effluent and the surface of the needle-like electrode 16.

Figure 3:
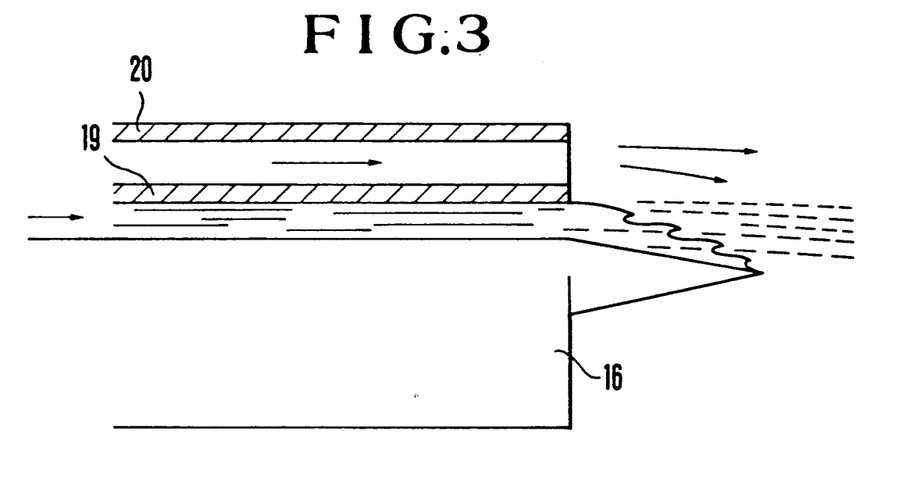
FIG. 3 is a further enlarged sectional view of the tip of the needle-like electrode portion shown in FIG. 2A.
Figure 4:
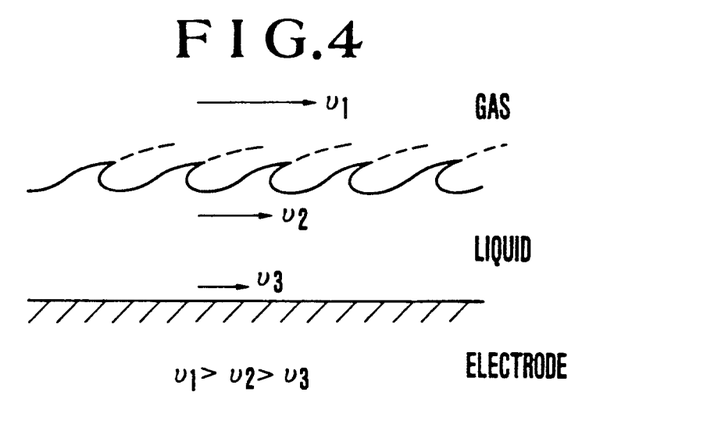
FIG. 4 is an explanatory view for the effect of splashing a liquid.

As shown in FIGS. 3 and 4, if $v_2 > v_3$, the evaporation and splashing of the liquid at the surface thereof is accelerated, whereby droplets are generated. At this time, the ions with the same polarity as that of the needle-like electrode 16 gather on the surface layer of the effluent, while the opposite charge gathers near the surface of the needle-like electrode 16. The droplets generated thus contain a large amount of ions, and the evaporation of the ions is accelerated owing to the combination with the Coulomb repulsion between the respective ions. The charge opposite to that of the needle-like electrode 16 which gathers near the surface thereof disappears on the surface of the electrode. In FIG. 4, $v_1$ is the flow rate of the sample sending gas.

As a result, ionization is effectively and stably effected even if a relatively large amount of effluent is introduced into the ion extractor 6'.

Figure 5:
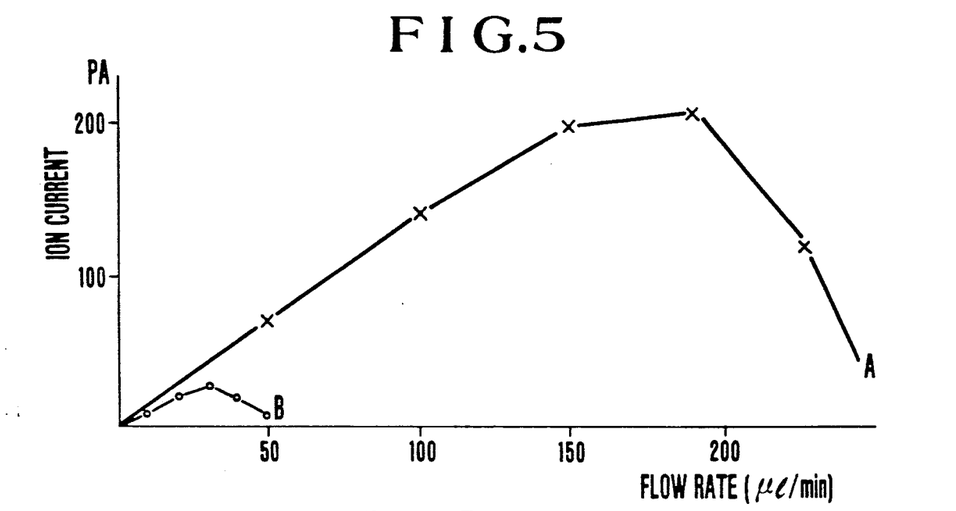
FIG. 5 is a drawing which shows a relationship between the amount of an effluent and the value of an ion current.

FIG. 5 is a drawing which shows a relationship between the amount of the effluent which flows into the ion extractor 6' and the value of an ion current. The conditions for obtaining the data shown in the drawing are as follows:

The diameter of the needle-like electrode 16 was 100 μm (0.1 mm), with the tip thereof being pointed by electrolytic polishing so that the radius thereof was several μm. Dry nitrogen gas was used as the sample sending gas, and the flow rate was set to 1 l/min. As shown in FIG. 2C, the length of projection at the tip of the needle-like electrode 16 was 5 mm, the external diameter and the internal diameter of the first tube 19 were 1 mm and 0.25 mm, respectively, and the external diameter and the internal diameter of the second tube 20 were 4 mm and 2 mm, respectively. The voltage applied to the needle-like electrode 16 was +3 KV.

In FIG. 5, a curve A represents the data obtained when the needle-like electrode 16 was present, and a curve B represents the data obtained when the needle-like electrode 16 was not present. It is found from these data that ionization is stably and effectively performed owing to the presence of the needle-like electrode 16 even if the flow rate is relatively high. On the other hand, when the needle-like electrode 16 is not present, the maximum flow rate is several tens of μl/mn. It is therefore found that the presence of the needle-like electrode 16 enables the achievement of stable and effective ionization even if the flow rate of the effluent is relatively high.

Figure 6:
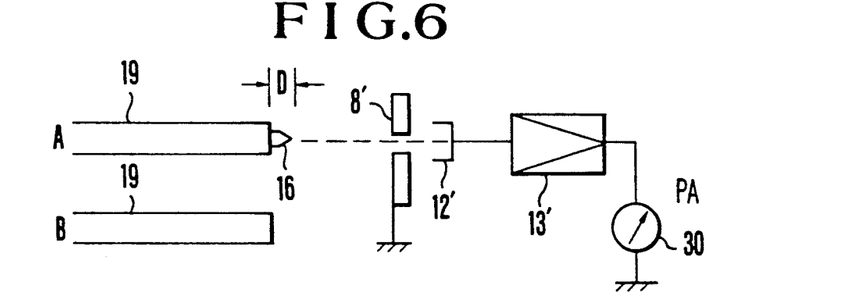
FIG. 6 is a drawing of the configuration of a system used for measuring an ion current.

FIG. 6 shows a system for measuring ion currents which was used for obtaining the data shown in FIG. 5. In the electrode, and character B denotes a case using no needle-like electrode. Reference numeral 8' denotes an extraction electrode; reference numeral 12' an ion detector; reference numeral 13' an amplifier; and reference numeral 30, an ammeter.

Figure 7:
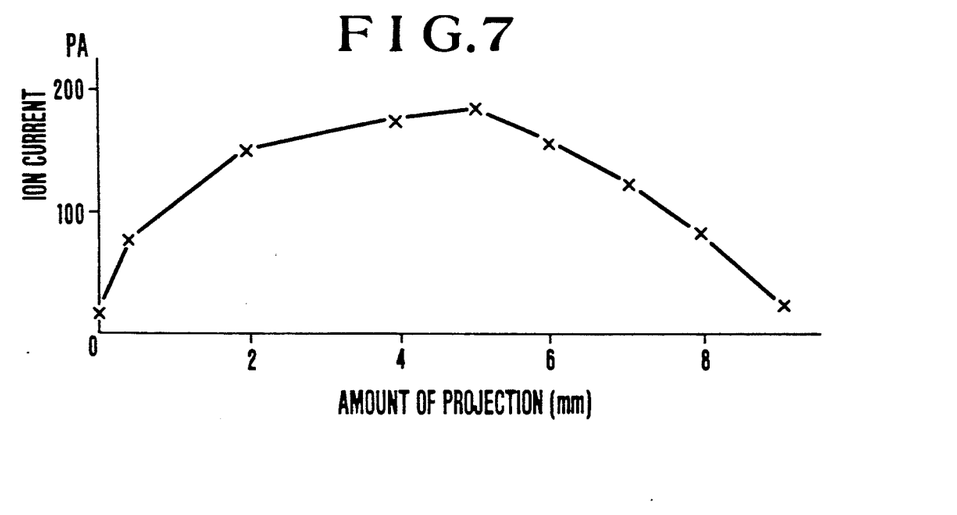
FIG. 7 is a drawing which shows a relationship between the amount of projection of a needle-like electrode and the value of an ion current.
Figure 8A:
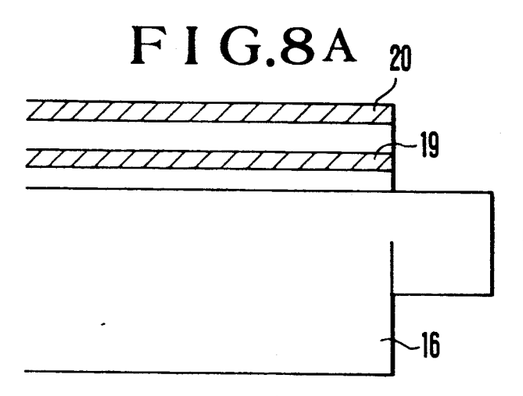
FIG. 8A is an enlarged sectional view of the tip of a nozzle portion in another embodiment.
Figure 8B:
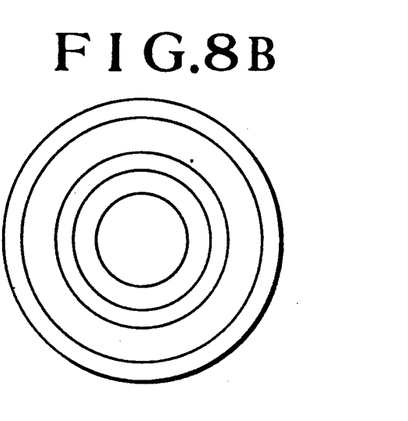
FIG. 8B is a right side view of the nozzle portion shown in FIG. 8A.

FIG. 7 shows a relationship of the value of ion current to the amount (length) of projection of the needle-like electrode 16 from the first tube 19. The data shown in the drawing was obtained by using the system shown in FIG. 6. It is found from the data that there is substantially no effect when the amount of projection is zero or extremely large.

Figure 9A:
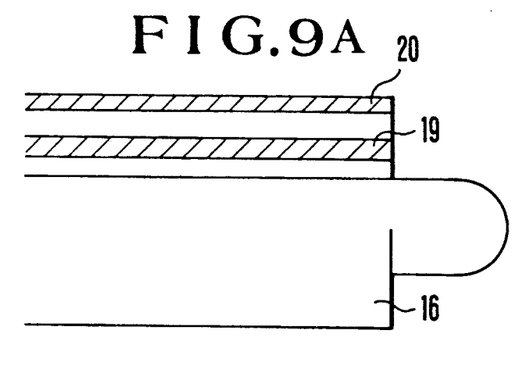
FIG. 9A is an enlarged sectional view of the tip of a nozzle portion in a further embodiment of the present invention.
Figure 9B:
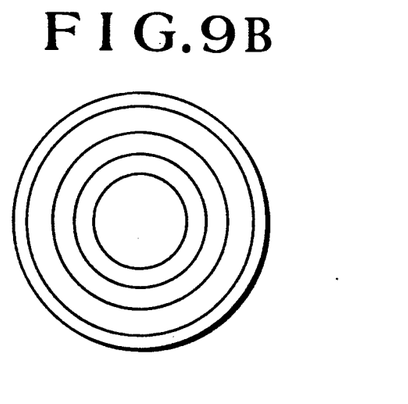
FIG. 9B is a right side view of the nozzle portion shown in FIG. 9A.
Figure 10A:
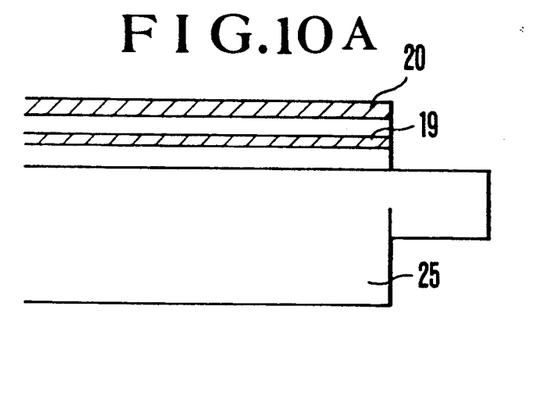
FIG. 10A is an enlarged sectional view of the tip of a nozzle portion in still a further embodiment.
Figure 10B:
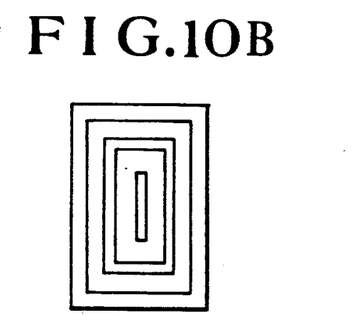
FIG. 10B is a right side view of the nozzle portion shown in FIG. 10A.

The tip of the needle-like electrode 16 may be sharp as shown in FIGS. 2A and 2C,
.1 flat as shown in FIGS. 8A, 8B, 10A and 10B, or round as shown in FIGS. 9A and 9B. In addition, the sectional forms of the needle-like electrode 16 and the first and second tubes 19 and 20 may be circular as shown in FIGS. 8A, 8B, 9A, 9B or rectangular as shown in FIGS. 10A, 10B.

Figure 11:
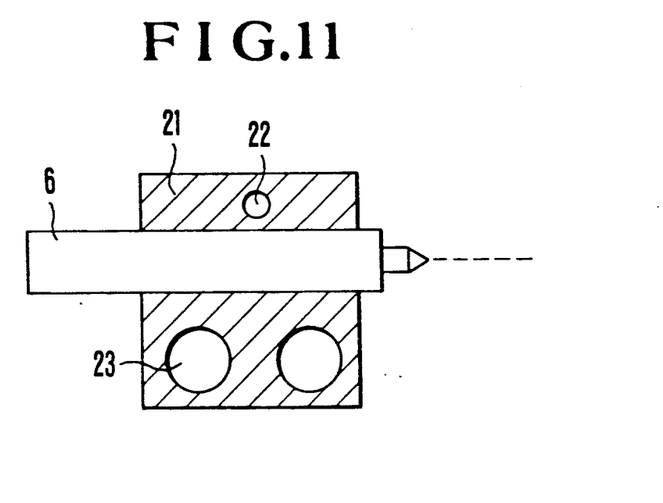
FIG. 11 is a sectional view of an embodiment of a heater.
Figure 12:
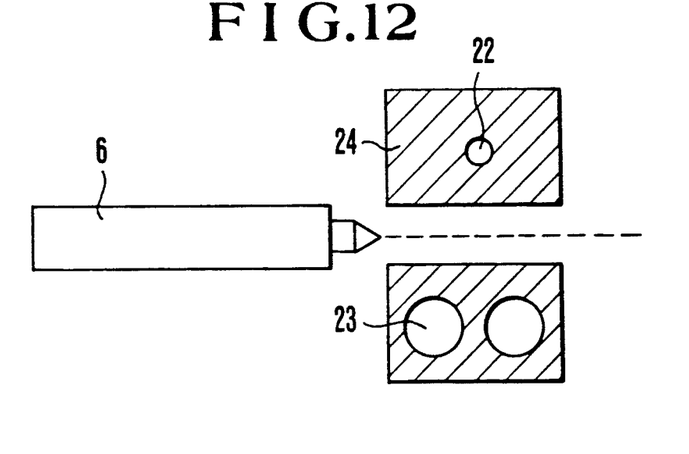
FIG. 12 is a sectional view of another embodiment of a heater.

Some samples are permitted to be heated to some extent. The heating enables an increase in the efficiency of evaporation of the solvent and thus enables an increase in the effect of extracting ions. FIGS. 11 and 12 respectively show methods of heating. FIG. 11 shows a method in which the whole of the nozzle portion 6 is surrounded by a heat block 21 which is heated by using cartridge heaters 23. FIG. 12 shows a method in which nebulized components are passed through a hollow heat block 24 containing cartridge heaters 23 so as to be evaporated.

In the drawings, reference numeral 22 denotes a thermocouple for measuring temperatures.

Since it is obvious that the above-mentioned embodiment can be modified into various forms within the scope of the substantial properties of present invention, the present invention should not be limited to the above embodiment.

What is claimed is:

1. An ion analyzer comprising an electrode having a surface onto which a liquid containing ions is introduced, means for supplying gas so that said liquid is moved while being held between said electrode and said gas, means for generating an electric field so that said ions are extracted, and means for detecting the ions extracted.

2. An ion analyzer comprising an electrode having a surface onto which a liquid containing ions is introduced, means for supplying gas so that said liquid is moved while being held between said electrode and said gas, means for generating an electric field so that said ions are extracted, means for mass-separating the extracted ions, and means for detecting the mass-separated ions.

3. An ion analyzer comprising a column for separating a sample liquid by an elvant flowing therethrough, means for extracting ions in an effluent from said column and means for detecting the extracted ions, said means for extracting ions comprising an electrode having a surface onto which said effluent is introduced, means for supplying gas so that said effluent is moved while being held between said electrode and said gas, and means for generating an electric field so that said ions contained in said effluent moved while being held between said gas and said electrode can be extracted.

4. An ion analyzer comprising a column for separating a sample liquid by an elvant flowing therethrough, means for extracting ions in an effluent from said column, means for mass-separating the extracted ions and means for detecting the extracted ions, said means for extracting ions comprising an electrode having a surface onto which said effluent is introduced, means for supplying gas so that said effluent is moved while being held between said electrode and said gas, and means for generating an electric field so that said ions contained in said effluent moved while being held between said gas and said electrode can be extracted.

5. An ion extractor comprising an electrode, means for introducing a liquid containing ions onto the surface of said electrode, means for supplying gas so that said liquid is moved while being held between said electrode and said gas, and means for generating an electric field so that said ions are extracted.

6. An ion extractor comprising an electrode, means for introducing a liquid containing ions onto the surface of said electrode, means for supplying gas so that said liquid is moved while being held between said electrode and said gas, and means for applying a voltage to said electrode so that said ions are extracted.

7. An ion extractor comprising an electrode, means for introducing a liquid containing ions onto the surface of said electrode, means for supplying gas so that said liquid is moved while being held between said electrode and said gas, and means for generating an electric field so that said ions are extracted, said gas supply means comprising means for setting the flow rate of said gas so that the speed of movement of said liquid at the surface thereof contacting with said gas is higher than that of said liquid at the surface thereof contacting with the surface of said electrode.

8. An ion extractor comprising an electrode, a first tube disposed so as to form a first gap around said electrode, a second tube disposed so as to form a second gap around said first tube, means for introducing a liquid containing ions into said first gap, means for supplying gas into said second gap, an ion extracting electrode disposed opposite to said electrode, and means for forming an electric field between said electrode and said extracting electrode so that said ions are extracted, said electrode projecting from said first tube so that said liquid is moved while being held between said gas and said electrode after it has passed through said first gap.

9. An ion extractor comprising a needle-like electrode, a first tube disposed so as to form a first gap around said needle-like electrode, a second tube disposed so as to form a second gap around said first tube, means for introducing a liquid containing ions into said first gap, means for supplying gas into said second gap, an ion extracting electrode disposed opposite to said needle-like electrode, and means for applying a voltage to said needle-like electrode so as to form an electric field between said needle-like electrode and said extracting electrode so that said ions are extracted, said electrode projecting from said first tube so that said liquid is moved while being held between said gas and said needle-like electrode after it has passed through said first gap, said gas supply means comprising means for setting the flow rate of said gas so that the speed of movement of said liquid at the surface contacting with said gas is higher than that of said liquid at the surface contacting with the surface of said electrode.

10. An ion extractor according to claim 8 further comprising means for adjusting the length of projection of said electrode from said first tube.

11. An ion extractor according to claim 9 further comprising means for adjusting the length of projection of said electrode from said first tube.

12. An ion extractor according to claim 5 further comprising means for heating said liquid.

13. An ion extractor according to claim 6 further comprising means for heating said liquid.

14. An ion extractor according to claim 7 further comprising means for heating said liquid.

15. An ion extractor according to claim 10 further comprising means for heating said liquid.

16. An ion extracting electrode apparatus comprising an electrode, a first tube disposed so as to form a first gap around said electrode and a second tube disposed so as to form a second gap around said first gap into which gas is supplied, said electrode projecting from said first tube.

17. An ion extracting electrode apparatus according to claim 12, wherein the amount of projection of said electrode from said first tube can be adjusted.

* * * * *